United States Patent
Baarman

(10) Patent No.: US 6,669,838 B1
(45) Date of Patent: Dec. 30, 2003

(54) APPARATUS FOR FILTERING AND STERILIZING WATER UTILIZING A TURBIDITY AND MICROORGANISM SENSING SYSTEM

(75) Inventor: David W. Baarman, Fennville, MI (US)

(73) Assignee: Access Business Group International LLC., Ada, MI (US)

( * ) Notice: Subject to any disclaimer, the term of this patent is extended or adjusted under 35 U.S.C. 154(b) by 0 days.

(21) Appl. No.: 09/974,940

(22) Filed: Oct. 11, 2001

Related U.S. Application Data

(63) Continuation-in-part of application No. 09/596,416, filed on Jun. 12, 2000, now Pat. No. 6,451,202.
(60) Provisional application No. 60/140,090, filed on Jun. 21, 1999.

(51) Int. Cl.[7] .................. C02F 1/32; G01J 1/42
(52) U.S. Cl. .............. 210/85; 210/103; 210/295; 210/302; 250/435; 250/372
(58) Field of Search ............. 210/85, 97, 745, 210/103, 192, 295, 302; 422/24, 186.3; 356/51; 250/372, 435

(56) References Cited

U.S. PATENT DOCUMENTS

| | | | |
|---|---|---|---|
| 3,471,693 A | * 10/1969 | Veloz .................. 250/432 R |
| 3,586,862 A | 6/1971 | Topol |
| 3,775,013 A | 11/1973 | Simms |
| 3,838,282 A | 9/1974 | Harris |
| 3,880,526 A | 4/1975 | Kobayashi et al. |
| 3,892,485 A | 7/1975 | Merritt et al. |
| 4,017,734 A | 4/1977 | Ross |
| 4,061,922 A | * 12/1977 | Last ................... 250/461.1 |
| 4,072,424 A | 2/1978 | McMullan et al. |
| 4,103,167 A | 7/1978 | Ellner et al. |
| 4,152,070 A | 5/1979 | Kushner et al. |
| 4,165,463 A | 8/1979 | Bowen |
| 4,193,692 A | 3/1980 | Wynn |
| 4,201,916 A | 5/1980 | Ellner |
| 4,278,508 A | * 7/1981 | White et al. ............. 205/776.5 |
| 4,371,897 A | 2/1983 | Kramer |
| 4,437,007 A | 3/1984 | Koslow et al. |
| 4,710,643 A | 12/1987 | Schmukler et al. |
| 4,801,204 A | 1/1989 | Nakamura et al. |
| 4,885,471 A | 12/1989 | Telfair et al. |
| 5,012,809 A | 5/1991 | Shulze |
| 5,039,854 A | 8/1991 | Yip et al. |

(List continued on next page.)

FOREIGN PATENT DOCUMENTS

| | | |
|---|---|---|
| DE | 3821543 | 1/1989 |
| JP | 60088351 | 5/1985 |
| JP | 0352686 | * 3/1991 |
| JP | 04004050 | 1/1992 |
| JP | 05154278 | 6/1993 |
| RU | 2118946 | 9/1998 |

Primary Examiner—Terry K. Cecil
(74) Attorney, Agent, or Firm—Amy I. Ahn; Alticor Inc.

(57) ABSTRACT

An apparatus for filtering and sterilizing water utilizing a turbidity and microorganism sensing system. The apparatus includes a UV light source that emits UV and visible light and light sensors. The light sensors include visible light detectors and light pipes that are impregnated with a fluorescent dye to covert UV light to visible light. The turbidity level is assessed by the detection of visible light passing through the water flow path while the microorganism levels are assessed by the detection of visible light that has been converted from UV light passing through the water flow path. The light sensors are in communication with a microprocessor which evaluates the intensity of the visible light and UV light. The microprocessor compares these intensities to a UV and visible light intensity standard to determine whether the water has been properly filtered and irradiated.

12 Claims, 17 Drawing Sheets

U.S. PATENT DOCUMENTS

| | | |
|---|---|---|
| 5,140,168 A | 8/1992 | King |
| 5,210,595 A | 5/1993 | Devore et al. |
| 5,241,368 A | 8/1993 | Ponstingl et al. |
| 5,281,823 A | 1/1994 | Weltz et al. |
| 5,416,581 A | 5/1995 | Kanngiesser |
| 5,446,544 A | 8/1995 | Beers |
| 5,460,723 A * | 10/1995 | Bourbigot et al. .......... 210/639 |
| 5,485,541 A * | 1/1996 | Bigley et al. ............... 385/141 |
| 5,586,567 A | 12/1996 | Smith et al. |
| 5,589,935 A | 12/1996 | Biard |
| 5,591,978 A | 1/1997 | Kovalsky et al. |
| 5,818,063 A | 10/1998 | Wilhelmstätter et al. |
| 5,828,458 A | 10/1998 | Taylor et al. |
| 5,916,801 A | 6/1999 | LoPinto et al. |
| 5,939,727 A | 8/1999 | Sommer |
| 6,313,468 B1 * | 11/2001 | Wedekamp ................. 250/373 |

* cited by examiner

APPARATUS FOR FILTERING AND STERILIZING WATER UTILIZING A TURBIDITY AND MICROORGANISM SENSING SYSTEM

This application is a continuation-in-part of U.S. patent application Ser. No. 09/596,416 filed on Jun. 12, 2000, now U.S. Pat. No. 6,451,202 B1 which claims priority under 35 U.S.C. §119(e) to Provisional Application Serial No. 60/140,090 filed on Jun. 21, 1999. The entire contents of both are incorporated by reference.

FIELD OF THE INVENTION

The present invention relates generally to water treatment system (WTS) units, and more particularly, to WTS units which employ light sensors to determine when the WTS units are filtering and sterilizing water properly.

BACKGROUND OF THE INVENTION

Water treatment system (WTS) units often employ filters to remove particulates and employ reactors containing ultraviolet (UV) lamps to destroy microorganisms in water being treated. Filters are generally replaced when either the filters have treated a predetermined quantity of water or when the filters have been in a WTS unit for a predetermined length of time. Even if only a small amount of water has been filtered, microorganism growth over time in the filter makes filter replacement desirable.

Similarly, UV lamps or bulbs also must be replaced. As time passes, the light intensity from light sources, such as UV bulbs, diminishes resulting in water passing through a light reactor vessel receiving diminishing amounts of UV light dosage. Sensors are often used to directly sense the UV light intensity coming from the UV bulb. When the sensors determine that the intensity has decreased below a threshold value, a signal is often given off by the WTS unit advising a user that the UV bulb should be replaced.

Conventional light sensing systems have several shortcomings. First, it is possible that water of increased turbidity or dirtiness may accidentally reach the UV reactor. In such a case, the increased turbidity may prevent all the water passing through the reactor from receiving the minimally desired quantity of UV light dosage even though the UV bulb is emitting a sufficient intensity of light. Second, as the intensity of the UV bulb diminishes over time, the water may or may not receive a minimum desired dosage of UV light due to fluctuations in turbidity. If the water is quite clear, then microorganisms residing in the water will receive a sufficient dosage of UV light even if the intensity of the UV light has decreased. However, if increased particle turbidity exists, then under otherwise satisfactory UV light intensity output from the UV bulb, some microorganisms shaded by the turbidity may not receive the desired dosage.

Water treatment standards include a NSF standard 55 Class A. Standard 55 Class A requires that light intensity be sensed after passing through water which is being treated. This accommodates the changing turbidity in the water. However, to date, few if any WTS units meet this standard 55.

The present invention is intended to provide a method and apparatus for addressing these shortcomings.

SUMMARY OF THE INVENTION

The present invention includes an apparatus and method for filtering and sterilizing water using a turbidity and microorganism sensing system in a WTS. The sensing system includes a UV light source, a flow path through which water to be treated with UV light passes, and at least one light sensor which receives UV light having passed through the flow path. The light sensor includes a light pipe and a visible light detector which may be a photocell. The light sensor contains a fluorescent dye which causes UV light striking the light pipe to fluoresce and emit visible light. The visible light is sensed by the photocell. The light sensor is in communication with a microprocessor for processing the intensity of the UV light sensed by the light sensor, converting the sensed visible light intensity to a UV light intensity, and comparing the UV light intensity against a UV light intensity standard. Another aspect of the invention includes a light sensor located proximate to the UV light source to receive direct UV light intensity. This UV light sensor can be used as a UV light intensity standard. Another aspect of the invention includes a light sensor having no fluorescing action and, thus, only sensing visible light to determine turbidity levels. Another aspect of the invention includes an alarm for signaling that the difference in the sensed and standard UV light intensities is sufficiently large that the system is not functioning properly. The sounding of the alarm could represent either turbidity and/or a high amount of microbiologicals in the water. In yet another aspect of the invention, the system includes at least one valve which reacts to the difference between the UV light intensity standard and the sensed UV light intensity and adjusts the volume of water flowing through the WTS such that the amount of turbidity and microorganisms flowing through the system is regulated to a manageable level. The valve controls the contact time of the UV light through the water by regulating water flow and the UV dose delivered to the water.

BRIEF DESCRIPTION OF THE DRAWINGS

The invention will become readily apparent from the following description, pending claims, and accompanying sheets of drawings where:

DETAILED DESCRIPTION OF THE INVENTION

Figure 1:
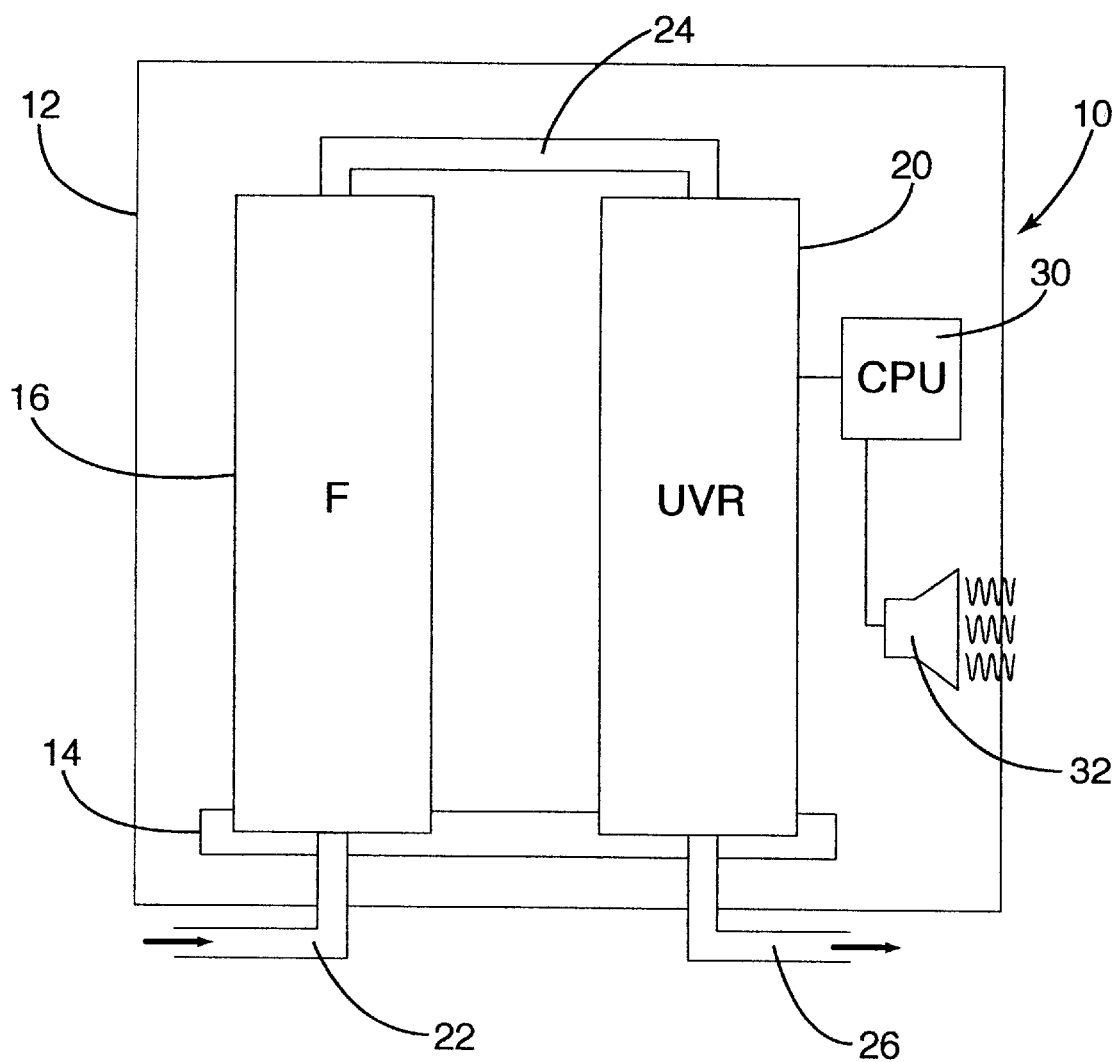
FIG. 1 is a schematic drawing of a water treatment system made in accordance with the present invention.

Referring to FIG. 1, an embodiment of a water treatment system (WTS) 10 unit is shown in accordance with the present invention. WTS 10 unit includes a housing 12 surrounding a base 14 which supports a filter assembly 16 and a UV light reactor 20. Water enters the WTS 10 through inlet conduit 22 and has particulates removed therefrom as it passes through filter assembly 16. Transverse conduit 24 transports the filtered water from filter assembly 16 to UV reactor 20. As water passes through UV reactor 20, the water is exposed to UV light which destroys microorganisms contained within the filtered water. If the water passing through the conduit 52 has high levels of turbidity, the turbidity may block some of the UV light from contacting the microorganisms in the water to successfully irradiate. Thus, the filter assembly's function in the present invention is to filter out particulates so that the microorganisms in the water receive an intensity of UV light sufficient to kill the microorganisms. Exit conduit 26 carries water away from UV reactor 20. This water leaving the WTS unit 10 has been filtered to remove particulates and treated with UV light to kill microorganisms in the water. A microprocessor or CPU unit 30 controls the operation of the WTS 10, including indicating when the WTS 10 is not filtering and sterilizing water at a desired level. When this substandard level is determined, an alarm 32 is activated. Alarm 32 may be an audible alarm or a visual alarm.

Figure 2:
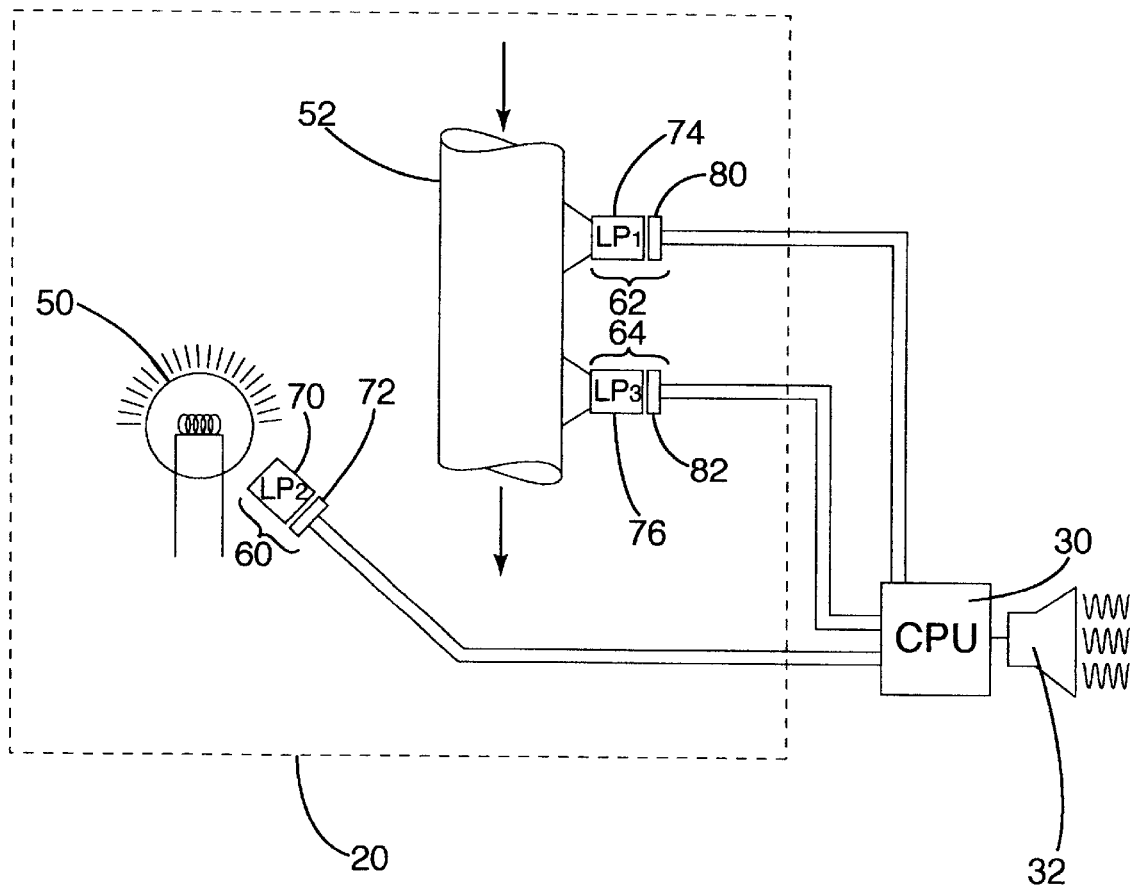
FIG. 2 is a schematic drawing of the UV reactor in FIG. 2 including UV lamp, water flow conduit and light sensors.

Referring now to FIG. 2, a schematic drawing of the UV reactor 20 in FIG. 1 is shown along with the microprocessor 30 and alarm 32. UV reactor 20 has a UV bulb 50 therein for irradiating water passing through a water flow path or conduit 52. Arrows indicate the direction of water flow. Water flow path or conduit 52 should allow UV light to pass readily through the conduit 52 to irradiate microorganisms in the passing water. Water conduit 52 may be made of materials such as quartz, TEFLON, TEFZEL, or any fluoropolymer or suitable UV transmitting glass or plastic. The volume of the conduit 52 is a factor determining the contact time of the UV light through the water. For example, a larger conduit provides a lesser contact time than a conduit having a smaller volume. Slower flow rates produce higher contact times allowing the UV light to penetrate the water flow path and perform as needed. The contact time determines the UV dose necessary to properly irradiate the water. The higher the contact time, the lower the UV dose.

One or more light sensors such as light sensors 60, 62, and 64 may be used to sense both visible and UV light intensity generated from the UV bulb 50. In the embodiment of FIG. 2, light sensors 62 and 64 receive UV light and potentially some visible light that has passed through the water conduit 52 while light sensor 60 acts as a reference sensor. A reference sensor is a light sensor that receives visible and/or UV light that has not passed through water. The visible and/or UV light that is sensed by the reference sensor is used as the visible and/or UV light intensity standard in a WTS. Those skilled in the art would recognize that the exact placement of the light sensors 60, 62, and 64 in the WTS 10 unit can vary and that the disclosed placement of the light sensors 60, 62, and 64 is by way of example only and should not be construed as a limitation of the present invention.

Figure 12:
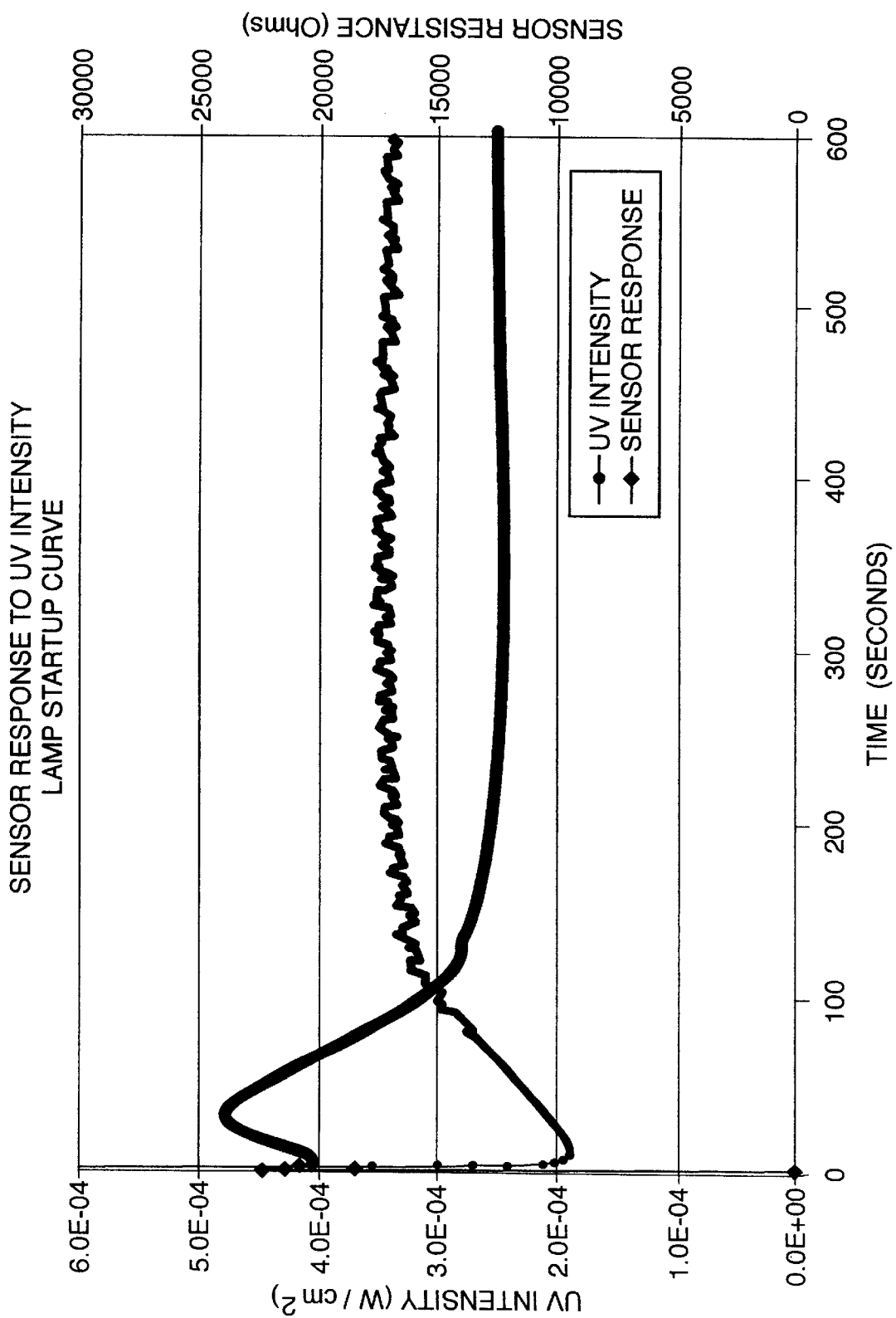
FIG. 12 is a graph illustrating the linear relationship between the UV light intensity and the sensed visible light created by fluorescing of UV light.

Light sensors 60, 62, and 64 are inexpensive as light pipes 70, 74, and 76 are made of acrylic and visible light detectors 72, 80, and 82 may be a simple photo diode, photocell, or cadmium sulfide cell (CDS cell). Light sensor 60 comprises a light pipe 70 and a visible light detector 72. Similarly, light sensors 62 and 64 incorporate light pipes 74 and 76 and visible light detectors 80 and 82. Light pipes 70, 74, and 76 contain a fluorescent material causing the light pipes 70, 74, and 76 to fluoresce and emit light in the visible range of the light spectrum when UV light is received by the light pipes 70, 74, and 76. Depending on the material chosen to make the light pipes 70, 74, and 76, different wavelengths of visible light are emitted. Light pipes 70, 74, and 76 can be made of V826 acrylic, which is generally clear, with a 1% ratio of fluorescent green dye dissolved or mixed in to the acrylic. The green dye is available from Uniform Color of Holland, Mich. under their designation 60-3170. This dye is adapted to fluoresce when placed in the pathway of UV light, such as UV light that is 254 nm in wavelength, resulting in the emission of visible light in the green range. The green color has proven to provide a very efficient transfer of UV light through light pipes 70, 74, and 76 while inhibiting the passage of most other colors. By utilizing a green fluorescent dye, it has been found that the intensity of visible light output from light pipe 70 is generally linearly proportional to the UV light created by the UV bulb 50 (See FIG. 12). Consequently, light sensors 60, 62, and 64 primarily sense the intensity of visible light created by fluorescing due to UV light striking the light pipes 70, 74, and 76 and not other visible light produced by the UV bulb 50. The use of a fluorescent dye in a light pipe allows measurement of visible light rather than UV light. Therefore, the present invention allows an inexpensive visible light detector and acrylic light pipe to be used rather than a more expensive UV light detector and quartz windows or light pipes. In another embodiment, light pipes 72, 74 and 76 can be made of different colored light pipes thus absorbing and emitting different ranges of light. These different ranges of light and their intensity can be analyzed by a microprocessor 30 to analyze the characteristics of the water such as turbidity which is not UV sensitive.

Figure 10:
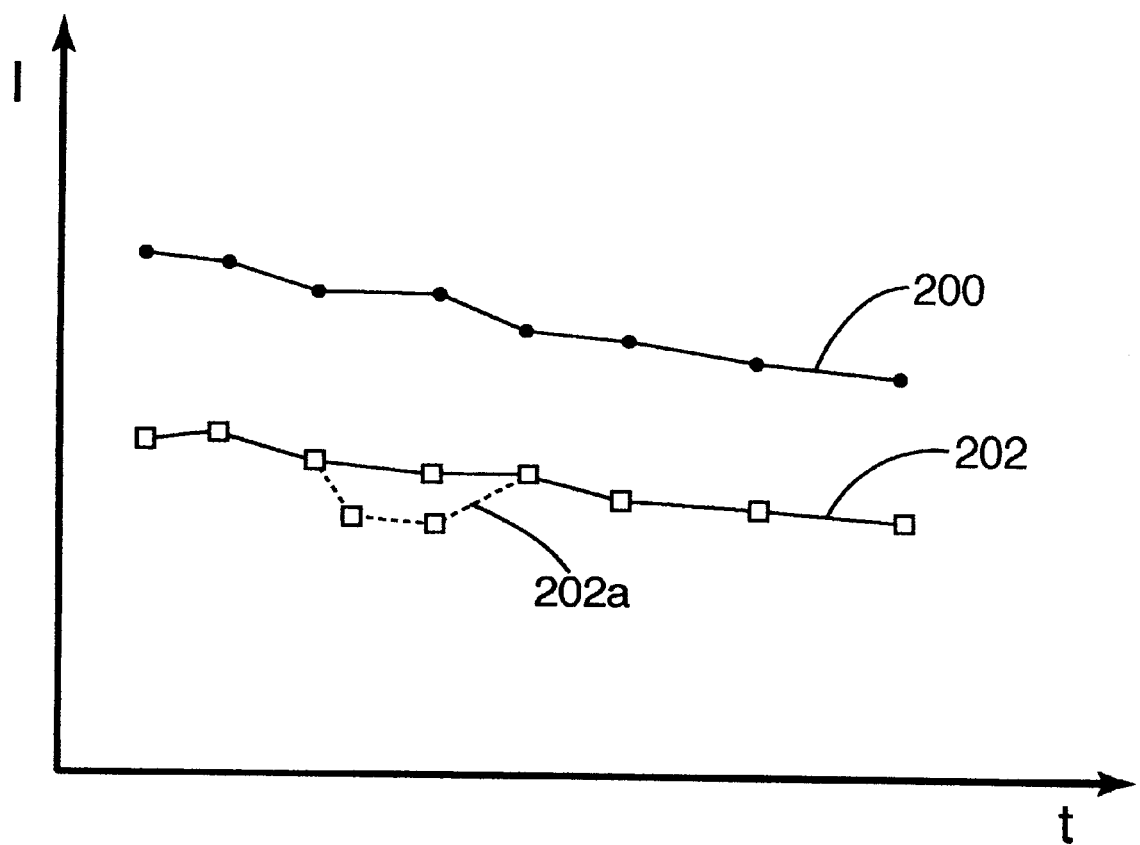
FIG. 10 is a graph illustrating measured UV light intensities over time sensed directly from a UV lamp and sensed from light passing through water in a flow path.
Figure 11:
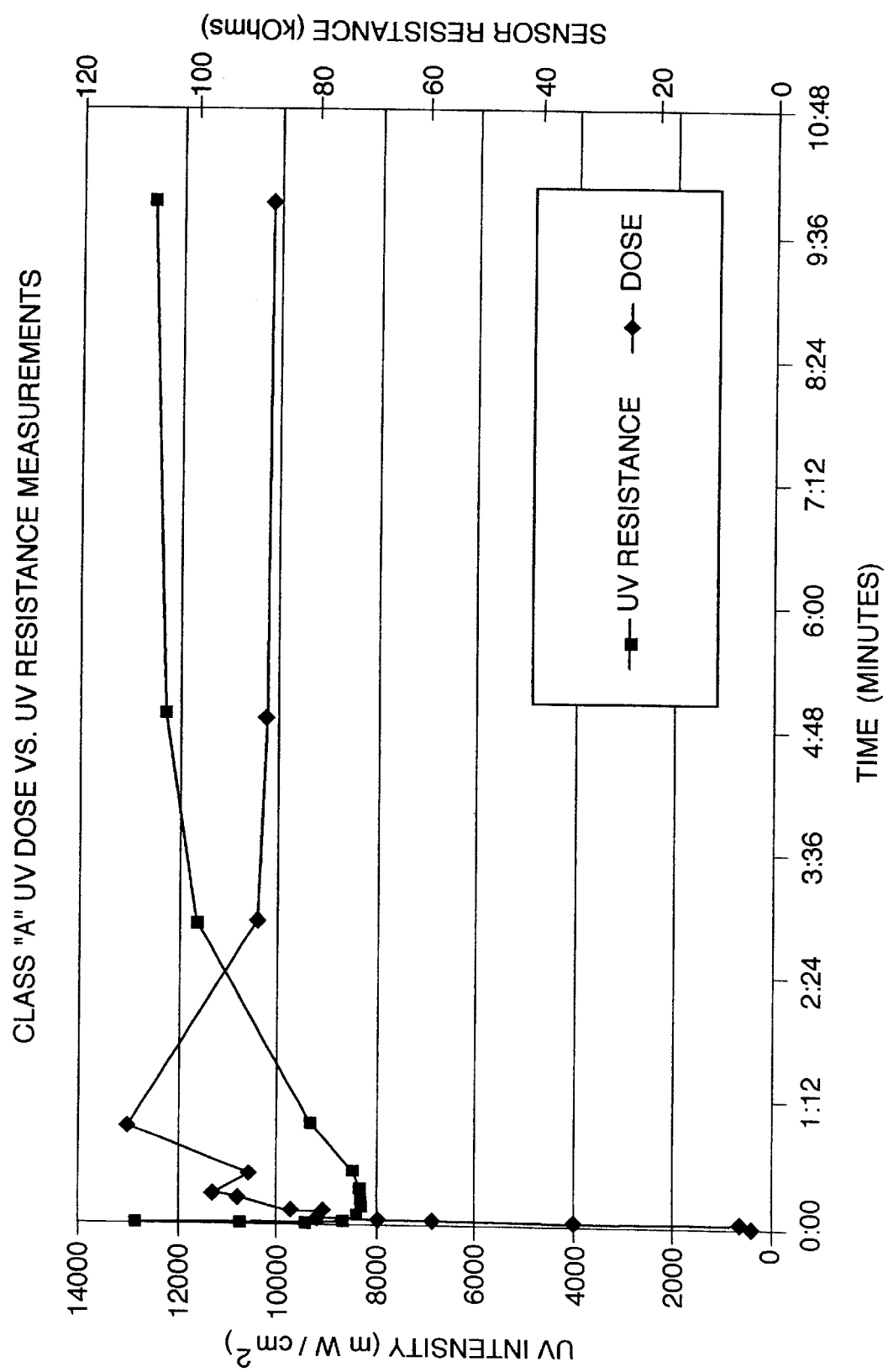
FIG. 11 is a graph depicting the relationship between the sensed UV light intensity and the UV dose in a water treatment system.

UV light that has fluoresced is received by visible light detectors 72, 80, and 82 which direct this visible light output to a microprocessor 30. Microprocessor 30 receives and processes the output light intensity received by the visible light detector 72 and compares this base value against the UV light intensity sensed by visible light detectors 80 and 82. The light intensity produced by UV bulb 50 will diminish over time, as shown in the graph of FIG. 10. Top line 200 indicates UV light intensity sensed from light sensor 60 over time. The relative UV light intensity detected by light sensor 62 or 64 is shown by bottom line 202. The relative difference in sensed UV light intensities is related to the turbidity and microorganisms in water passing through the conduit 52. If too great a difference is sensed, the microprocessor 30 will activate the alarm 32 to indicate to a user that water dispensed from the WTS 10 should not be consumed until the alarm 32 shuts off indicating that the water is desirably treated. Line 202a shows the result of sudden increased turbidity and microorganisms in the water with resulting lowering of sensed UV light intensity. When the difference between the sensed UV light intensity of sensor 60 and sensor 62 or 64 is too great for too long of time, it is time to replace UV bulb 50 and/or the filter 16.

Alternatively, the sensed UV light intensity from light sensor 62 and/or 64 can be compared to a UV light intensity standard of 38,000 μW. Using dose testing, the actual UV dose delivered is tested and recorded. The UV light intensity standards for the minimum UV dose required to properly irradiate the microorganisms in the water plus a safety margin are stored in a look up table which is preprogrammed in the microprocessor 30. Accordingly, the look up table will include corresponding volume, time, and UV light intensity values. If the difference in UV light intensity sensed by light sensors 62 and 64 is greater than the corresponding values in the look up table, an audible or visual alarm 32 will be activated, indicating to the user that the level of turbidity and microorganisms is substandard and, thus, the water has not been properly filtered and sterilized.

Figure 3:
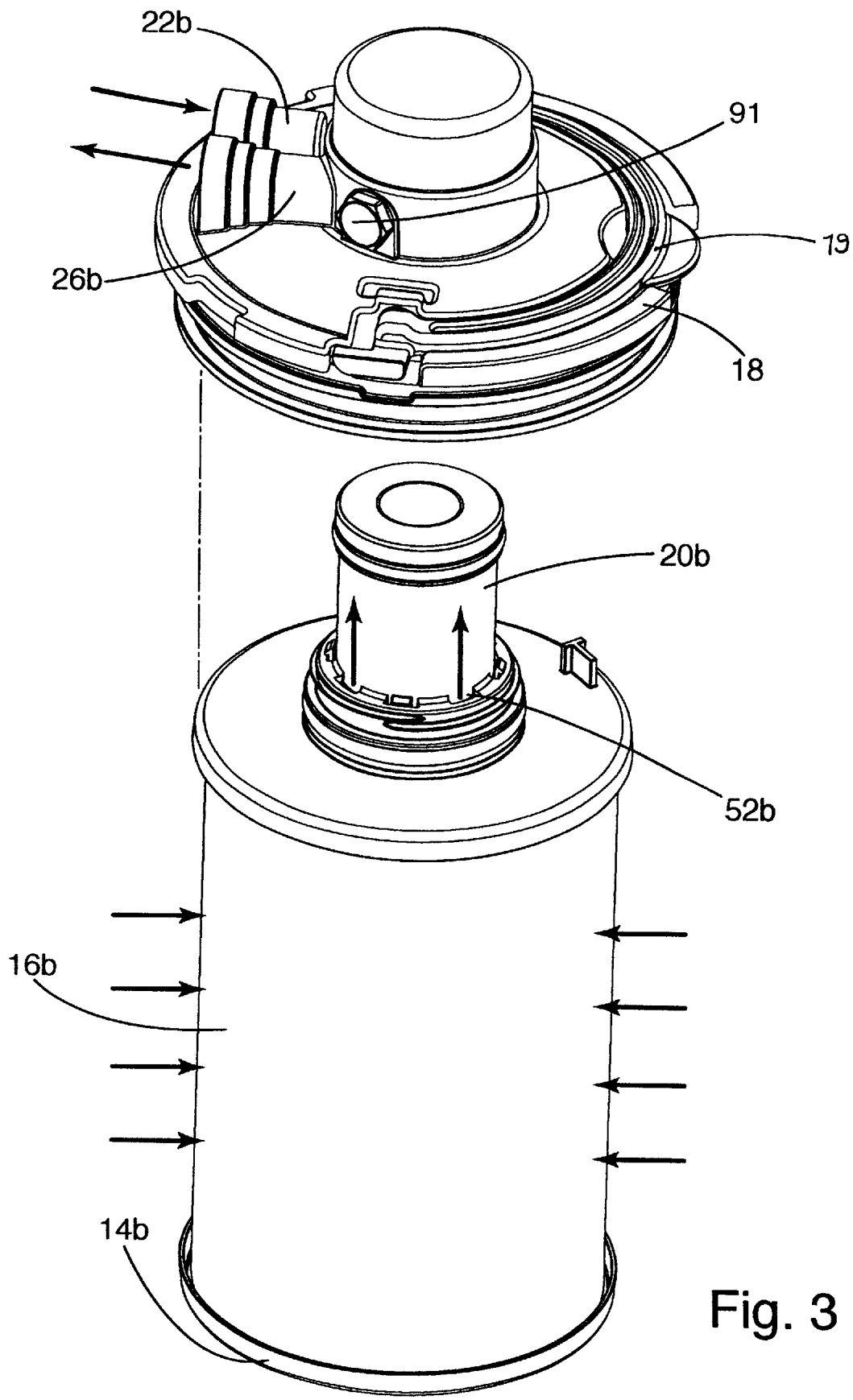
FIG. 3 is an exploded view of a filter assembly and a filter bracket used in another embodiment of a water treatment system.

Now referring to FIG. 3, another embodiment of a filter assembly 16b and UV reactor 20b for use in a WTS in accordance with the present invention is shown. The reference numerals 16b and 20b generally designate yet another embodiment of the present invention. Since filter assembly 16b and UV reactor 20b are similar to the previously described filter assembly 16 and UV reactor 20, similar parts appearing in FIGS. 3–7 are represented by the same, corresponding reference numeral, except for the suffix "b" in the numerals of FIGS. 3–7. The filter assembly 16b and UV reactor 20b are disposed within a WTS housing and mounted to a base 14b. The filter assembly 12b is coupled to a filter bracket 18 that has a pivotal handle 19 for facilitating removal of the filter assembly 16b when the filter 16b requires replacement. Arrows in FIG. 3 show the flow of water. Water flows in the inlet conduit 22b and downward towards the filter 16b surrounding the filter and passing through the filter 16b. When the filter bracket 18 is placed onto the filter assembly 16b the flow path for the inlet conduit 22b is kept separate from the flow path of the outlet conduit 26b by virtue of partitions located on the underside of the filter bracket 18.

Figure 4:
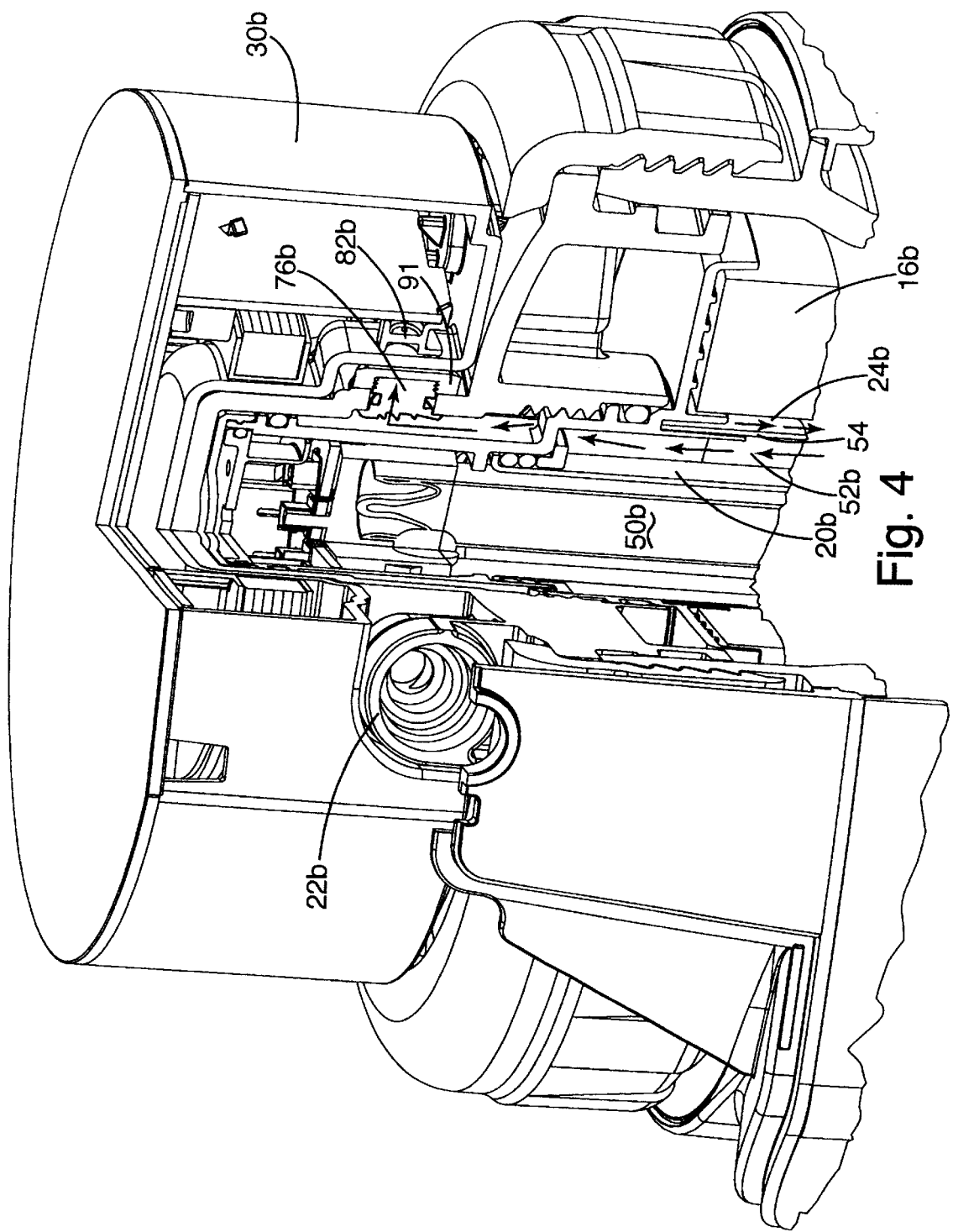
FIG. 4 is a partial cross sectional view of the filter assembly and filter bracket in FIG. 3

Referring now to FIG. 4, a partial cross section of the filter assembly 16b, filter bracket 18, and a microprocessor 30b that is located over the filter bracket 18 are shown. The filter assembly 16b surrounds a cylindrical reflector 54 which surrounds a UV reactor 20b. The reflector 54 is made of aluminum or a material that reflects rather than absorbs UV light. The reflector and the inner surface of the filter assembly create a transverse conduit 24b which transports filtered water to the UV reactor 20b. Arrows in FIG. 4 show the direction of water flow. The reflector 54 and the outer wall of the UV reactor 20b form a water conduit 52b that transports water through the conduit 52b so microorganisms in the water can be irradiated. The UV reactor 20b is made of materials such as quartz, TEFLON, TEFZEL, or any fluoropolymer or suitable UV transmitting glass or plastic. After water has flowed through the filter assembly 16b and has particulates removed therefrom, water is subjected to the UV light emanating from the UV bulb 50b. The UV bulb 50b irradiates microorganisms in the water. The upper-most arrow in FIG. 4 shows the general direction of the UV light which irradiates the microorganisms in the water and which passes through a light pipe 76b and is detected by a light detector 82b. Water that has been filtered and irradiated now leaves the WTS through the exit conduit 26b. Note that in this embodiment light pipe 76b and corresponding visible light detector 82b are the only light pipe and visible light detector incorporated in the WTS 10 to monitor turbidity and microorganism levels. However, it is envisioned that additional light pipes and photocells may be used to monitor turbidity and microorganism levels.

Figure 5A:
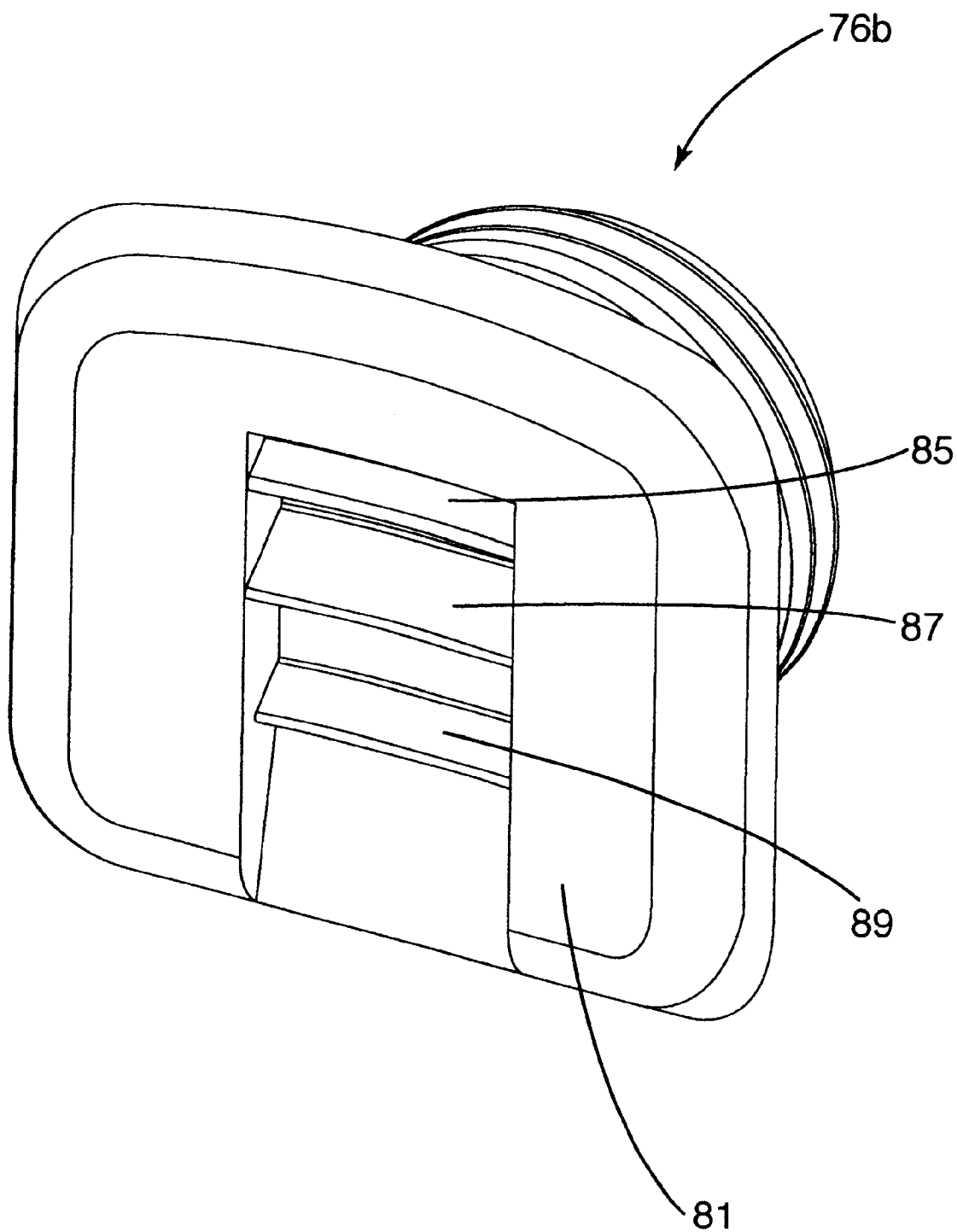
FIGS. 5a–5d are front perspective, rear perspective, side, and top views respectively of the light pipe as shown in FIG. 4.
Figure 5B:
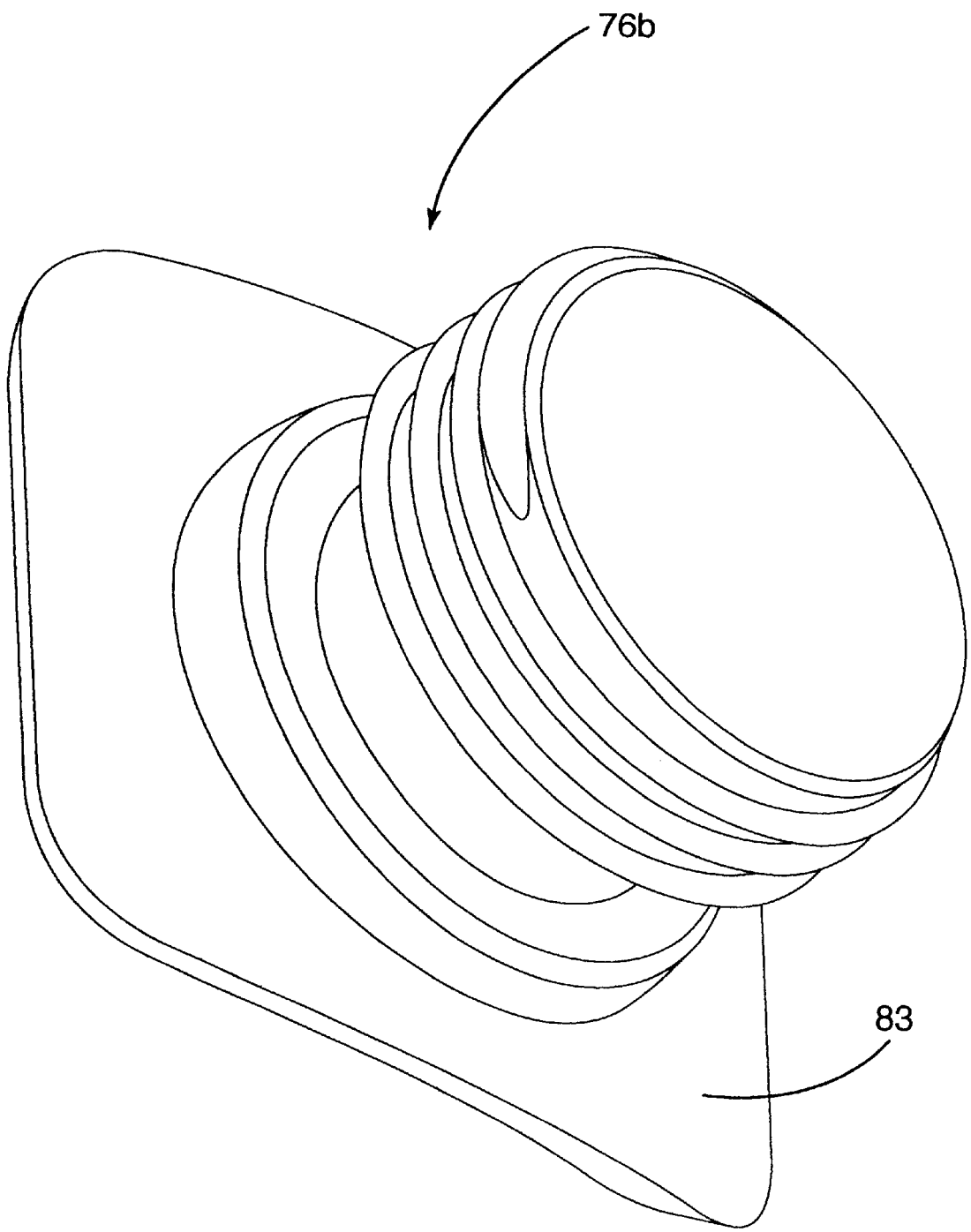
Figure 5C:
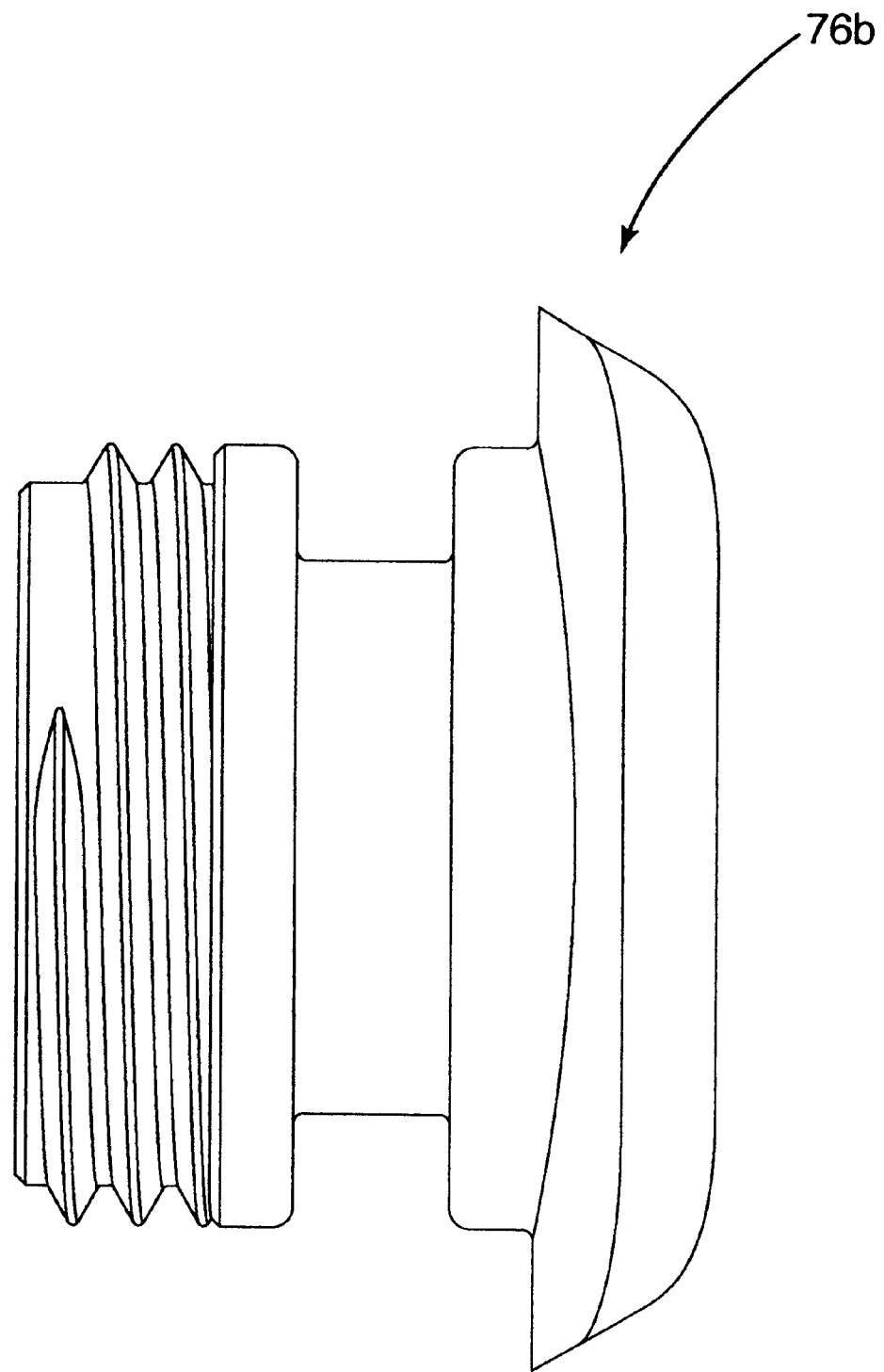
Figure 5D:
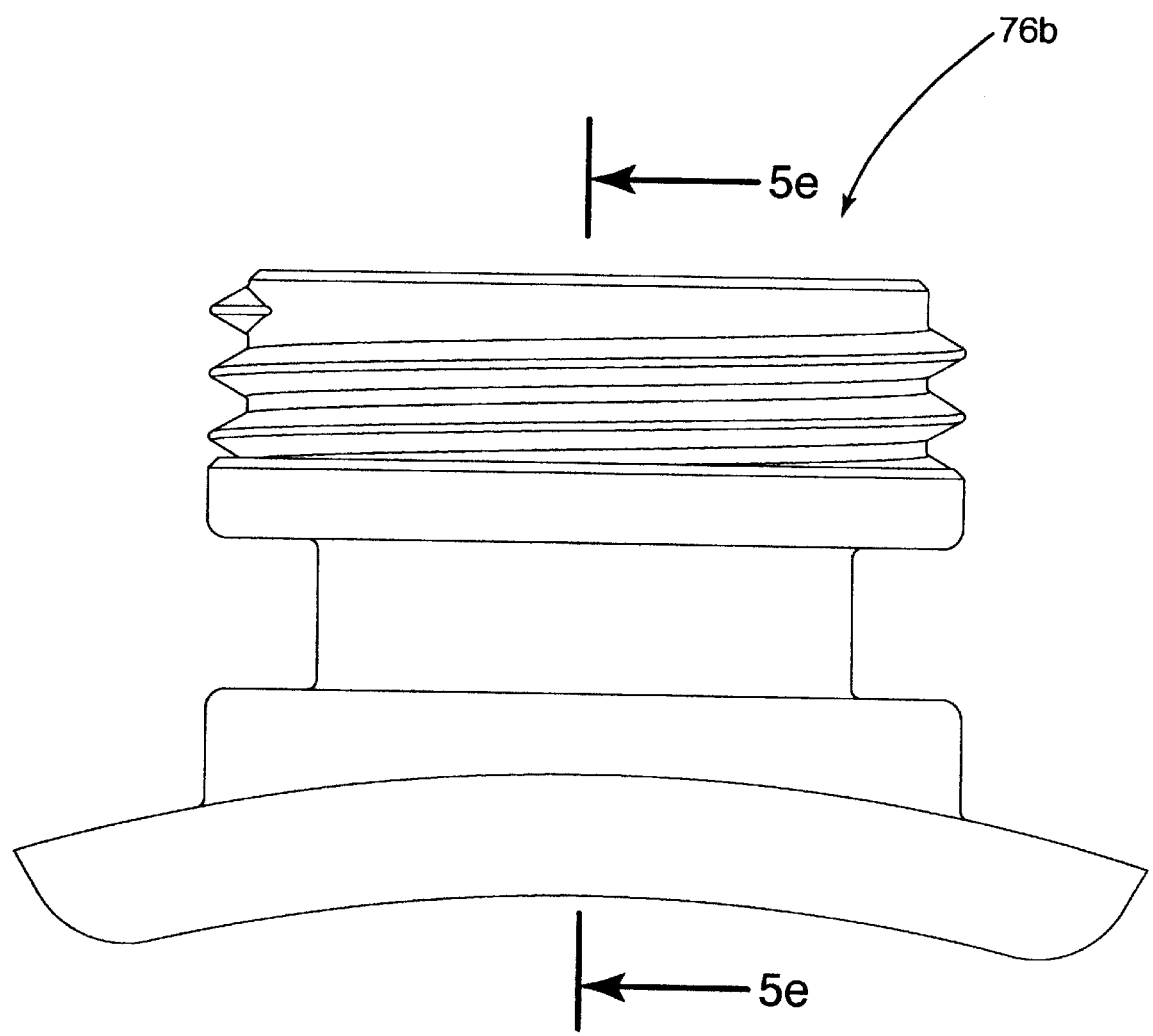
Figure 5E:
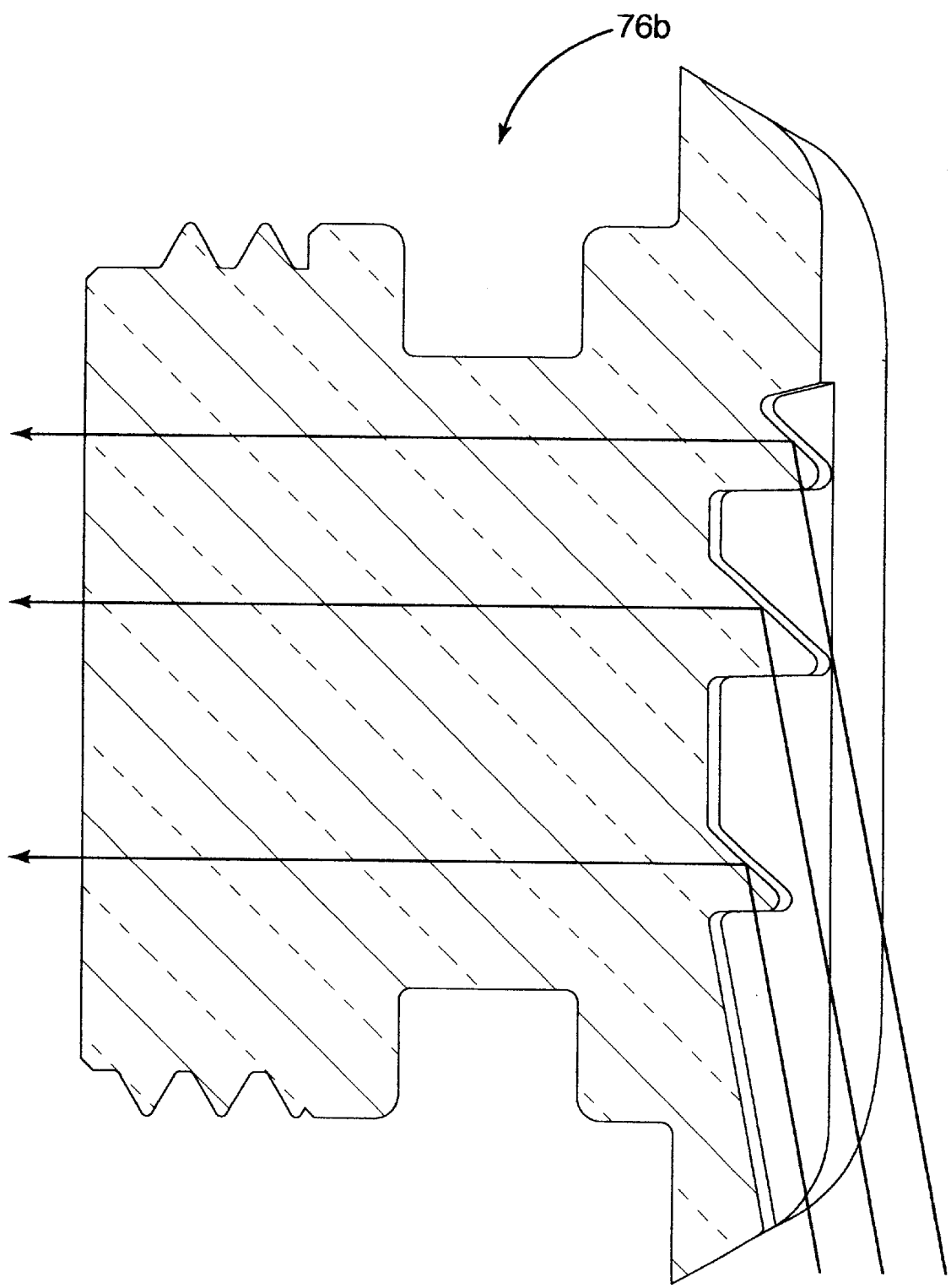
FIG. 5e is a cross sectional view of the light pipe in FIG. 5d taken along line 5e—5e.
Figure 6A:
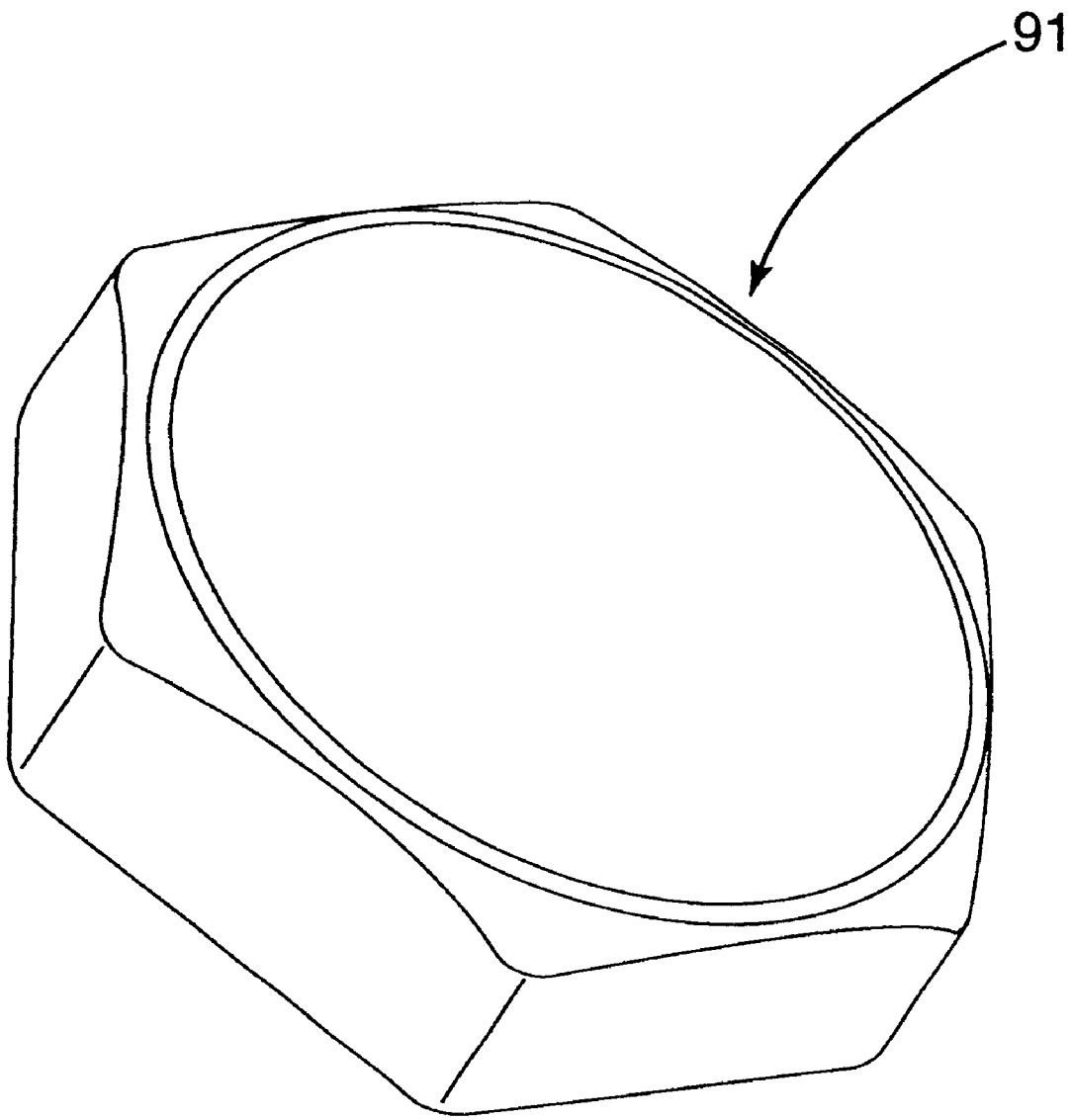
FIGS. 6a & 6b are enlarged front perspective and rear perspective views of a light pipe cover that can be attached to the light pipes in FIGS. 5a–5d.
Figure 6B:
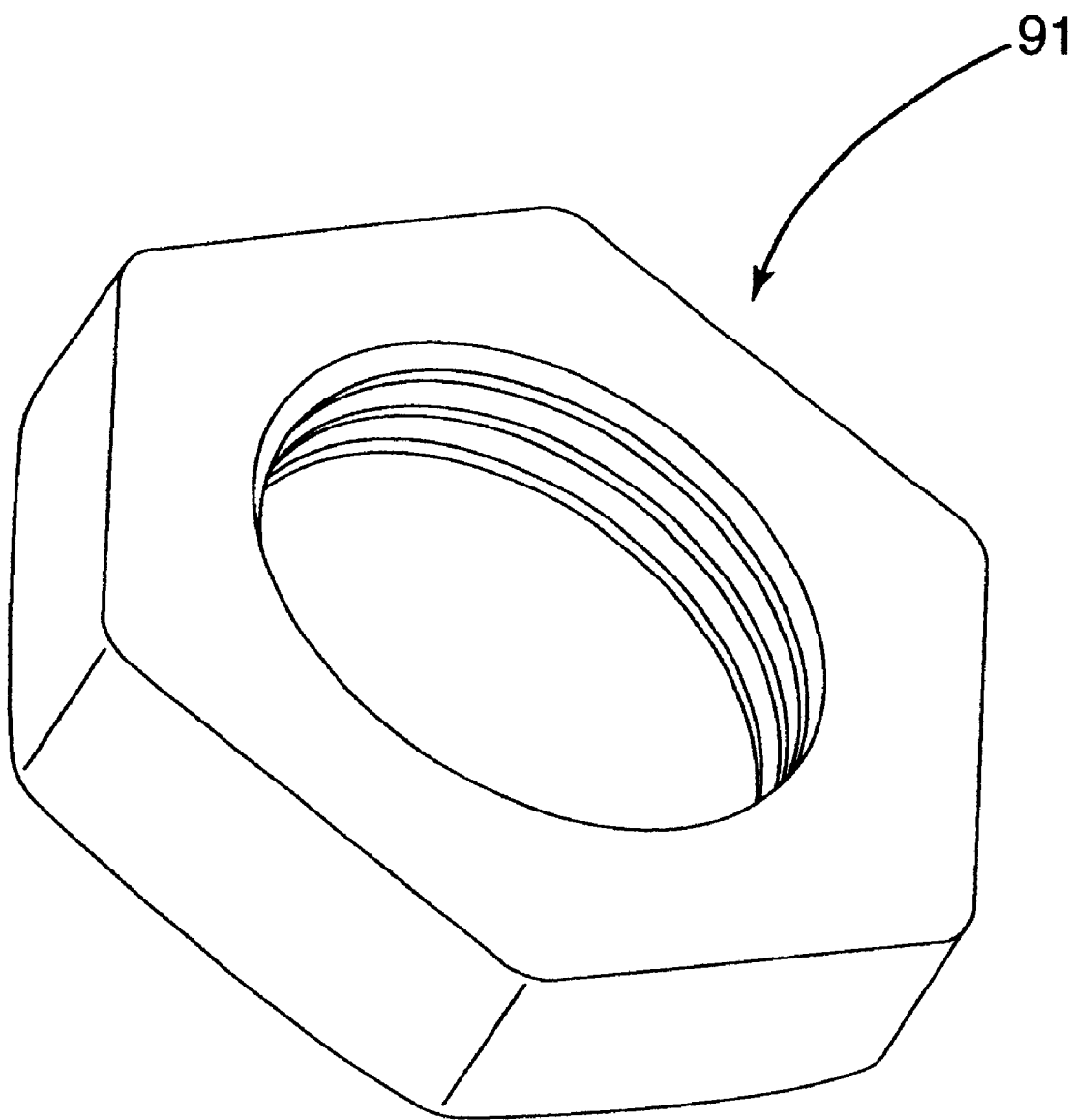
Figure 7:
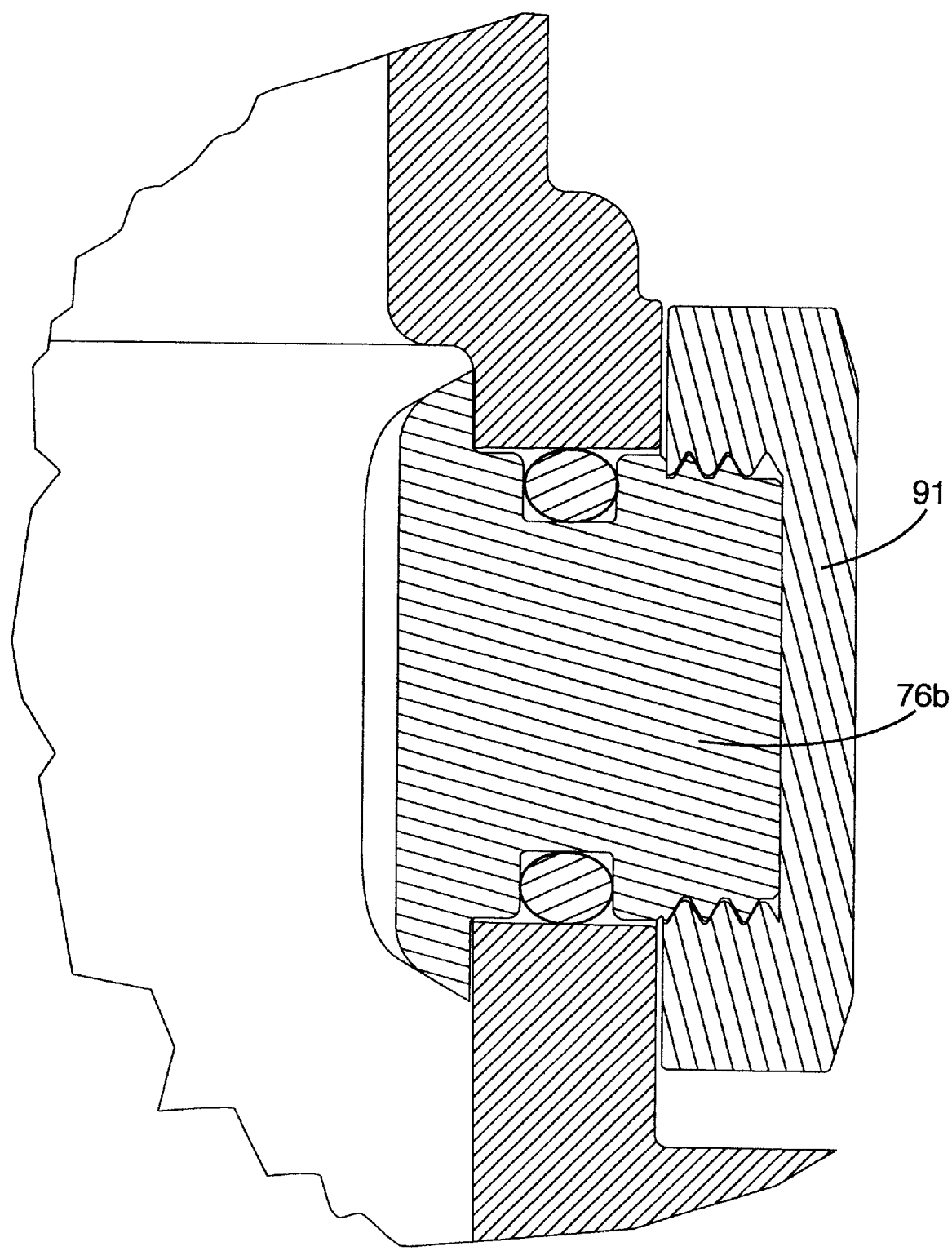
FIG. 7 is an enlarged cross sectional view of the light pipe, with a light pipe cover attached thereto, taken along line 5e—5e.

Light pipe 76b is configured according to FIGS. 5a–5e. Light pipe 76b has an interior surface 81 that is exposed to water flowing up and between the filter 16b and the UV reactor 20b. The interior surface 81 is configured by optics design and includes receiving surfaces 85, 87, and 89. The receiving surfaces 85, 87, and 89 of light pipe 76b are angled and/or curved to accept light from the mid portion of the light source. The arrows in FIG. 5e show the general direction light would travel when passing through the light pipe 76b. Because exposure to fluorescent dyes are not desirable for treated water, the fluorescent dye of the present invention may be dissolved or contained in the exterior surface 83 of the light pipe 76b where water does not come into contact with the dye. The fluorescent dye can also be dissolved or contained in a separate device connected to the light pipe 76b in a manner such that the dye containing device is not subjected to water. One example as shown in FIGS. 6a and 6b is dissolving or containing the fluorescent dye in a light pipe cover 91 that can be coupled to the light pipe 76b as shown in FIG. 7. The light pipe 76b in FIGS. 5a–5e is disposed in the WTS to monitor the average intensity of the lamp and not focus on lamp filaments or the lamp ends where the UV light intensity may be severely limited. The material composition of the light pipe 76b and the light pipe cover 91 is similar to that described for light pipes 70, 74, and 76. Further, the incorporation of the fluorescent dye whether in the exterior 83 of the light pipe 76b or in a light pipe cover 91 functions to accomplish the same objects as disclosed in the first embodiment.

Referring again to FIG. 4, like visible light detectors 72, 80, and 82, visible light detector 82b may also be a simple photodiode, photocell, or CDS cell. Visible light detector 82b in this embodiment is located in the microprocessor 30b. Accordingly, the housing of the microprocessor 30b is generally transparent so that fluorescing light can be received and sensed by the visible light detector 82b therein. The microprocessor housing 30b can be made of the same material used for the water conduit 52b. Like the previously disclosed WTS 10, the microprocessor is in communication with an alarm and/or a valve system. Further, the action of the photocell in communicating with the microprocessor to activate an alarm or valve system is generally the same as that disclosed in the previous embodiment.

Using the previously disclosed embodiments to monitor the UV light source and the UV light intensity through the water flow path, both turbidity and absorption can be monitored but may not be differentiated. The alarm in these embodiments will detect turbidity and/or absorption. One of ordinary skill in the art will appreciate that turbidity is represented by a visible difference in the amount of visible light transmitted through the water. Absorption especially with microorganisms would not be measured by a turbidity sensor. Absorption can be indicated in a clear solution as it is the UV 254 nm being absorbed by microorganisms. With the filter 16 and 16b taking the turbidity to a reasonable level, the filter 16 and 16b opens up the water path clarity for a UV absorption measurement. If turbidity is not removed by the filter 16 and 16b, the light sensors 62 and 64 may still function as turbidity sensors. When turbidity is present, using both a visible turbidity sensor and an UV absorption sensor provides information to the microprocessor 30 and 30b which can differentiate between the presence of turbidity and the presence of microorganisms within the water path. Accordingly, any of the disclosed embodiments can incorporate additional light sensors having light pipes that lack a fluorescent dye in conjunction with light sensors having fluorescing properties. If such visible light sensors are incorporated, it is envisioned that the visible light emitted by the UV bulb is sensed by the non-fluorescent light pipes and UV light emitted by the UV bulb is sensed by light pipes containing a fluorescent dye. Accordingly, it is not necessary for the microprocessor to determine what fraction of the UV light intensity output is a measurement of absorption and what fraction is a measurement of turbidity.

Figure 8:
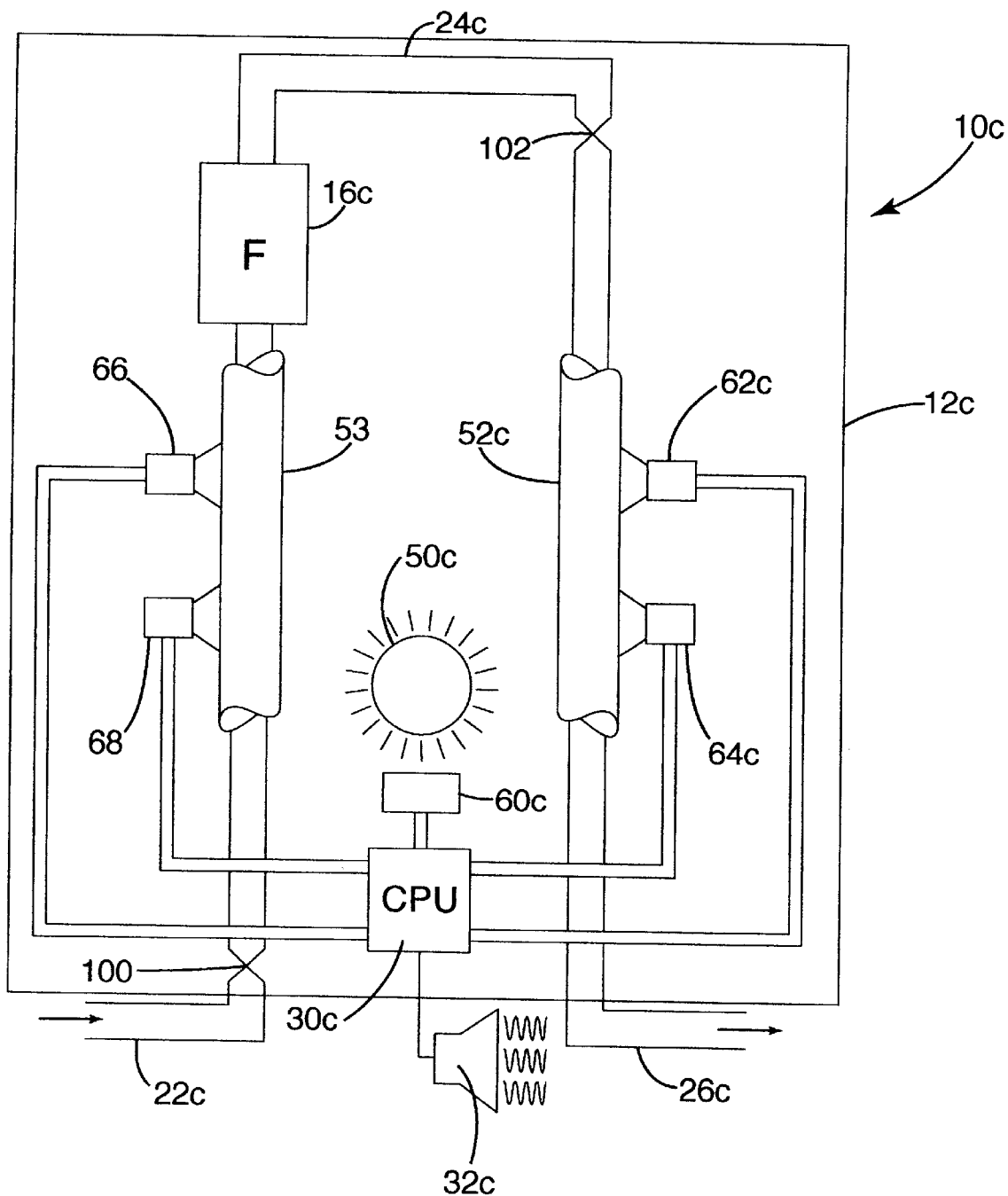
FIG. 8 is a schematic drawing of another water treatment system having a plurality of light pipes and flow paths.

Referring now to FIG. 8, a plurality light sensors 60c, 62c, 64c, 66 and 68 are incorporated in a WTS unit 10c to measure UV light absorption before the water is filtered and after the water is filtered. The reference numeral 10c generally designates yet another embodiment of the present invention. Since WTS 10c is similar to the previously described WTS 10, similar parts appearing in FIG. 8 are represented by the same, corresponding reference numeral, except for the suffix "c" in the numerals of FIG. 8. This embodiment provides an assessment of the amount of turbidity that has been removed by the filter. Because turbidity can block UV light from penetrating the microorganisms, UV measurement directly before and after water passes through the filter can indicate whether particulates have been adequately removed. Structuring a WTS unit to detect turbidity and microorganism levels before and after water has passed through the filter 16c allows one to assess the filter's 16c performance over its life, indicates when it has reached the end of its life and report accordingly.

FIG. 8 also incorporates control valves 100 and 102 to adjust the volume of water flowing from predetermined points in the WTS unit 10c. Control valves 100 and 102 may be located in at least two locations: the first valve 100 being located upstream of the second water conduit 53 to control the volume of water entering the second water conduit 53; and the second valve 102 being located downstream from the filter assembly 16c and upstream from the water conduit 52c to control the volume of water entering water conduit 52c. Additional valves may be incorporated near the exit conduit 26c and in the inlet conduit 22c of the WTS unit 10c such that the volume of water entering the WTS unit 10c is controllable. In this embodiment, if turbidity levels in the water flowing pass valve 100 is substandard as determined by the microprocessor 30c, then valve 100 will cut off or limit the supply of untreated water into the WTS unit 10c until a user of the WTS unit 10c replaces the filter 16c or the UV light bulb 50c. The valves 100 and 102 control the contact time through regulating the water flow by knowing the dose delivered to the water. The use of the valves 100 and 102 also allow the WTS unit 10c to shut off and the alarm to sound if the water is unsafe to drink. Again, it is the minimum UV dose level that the light sensors 60c, 62c, 64c, 66, and 68 are calibrated against to determine the alarm and valve shut off threshold.

Figure 9:
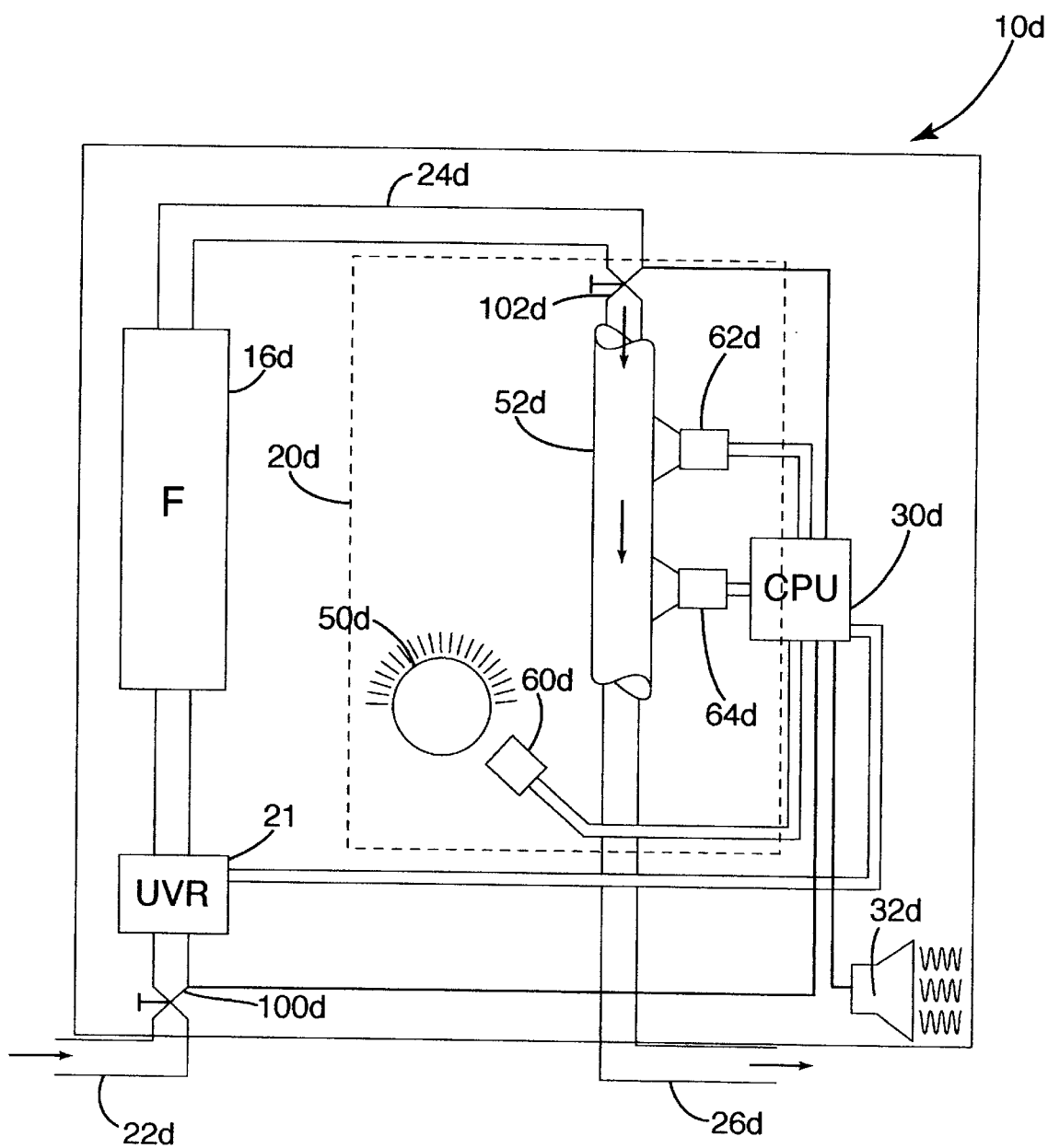
FIG. 9 is a schematic drawing of yet another water treatment system having two UV reactors.

FIG. 9 shows a modified version of the WTS unit of FIG. 8. The reference numeral 10d generally designates yet another embodiment of the present invention. Since WTS 10d is similar to the previously described WTS 10 and 10c similar parts appearing in FIG. 9 are represented by the same, corresponding reference numeral, except for the suffix "d" in the numerals of FIG. 9. The WTS 10d unit in FIG. 15 incorporates a second UV reactor 21. The second UV reactor 21 is the same as UV reactor 20d but is located upstream of UV reactor 20d.

One method of testing the accuracy of UV light absorption measured by the system is to use benzoic acid, which is a chemical that absorbs UV light much like DNA. A sample of deionized water is run through the WTS to set the reference. Using a laboratory UV vis, the level of absorption using concentrations of Benzoic Acid is determined by establishing samples for testing (1-2-3% etc.) The samples are then tested through the WTS and the microprocessor reads the sensors and builds the table. This establishes the initial table stored within the microprocessor allowing for the level of accuracy needed in the absorption sensor. Once the amount of microorganisms present in the sampled water is determined by use of UV light sensors, the same amount of benzoic acid is disposed in deionized water and that water is passed through the UV reactor. The UV light intensity with the benzoic acid in the water should be the same value as the UV light intensity determined in the sampled water. With very low cost sensors, one can established <1% absorption measurements.

While in the foregoing specification this invention has been described in relation to certain preferred embodiments thereof, and many details have been set forth for the purpose of illustration, it will be apparent to those skilled in the art that the invention is susceptible to alteration and that certain other details described herein can vary considerably without departing from the basic principles of the invention.

What is claimed:

1. A turbidity and microorganism sensing system in a water treatment system comprising:

a filter filtering water flowing through a water flow path;

a UV light source irradiating water flowing through the water flow path;

a first light sensor wherein the first light sensor senses the intensity of UV and visible light emitted from the UV light source that radiates through the water flow path;

a reference light sensor located proximate to the UV light source wherein the reference light sensor senses the intensity of UV and visible light emitted from the UV light source that has not radiated through the water flow path; and a microprocessor in communication with the first light sensor and the reference light sensor, and configured such that the differences in sensed UV light intensities are utilized for evaluating microorganism levels, and the differences in sensed visible light intensities are utilized for evaluating turbidity levels in water flowing through the system.

2. The system of claim 1 wherein:

the first light sensor includes a water exposed surface and a non-water exposed surface wherein the non-water exposed surface contains a fluorescent dye.

3. The system of claim 1 wherein:

the first light sensor includes a light pipe wherein the light pipe contains a fluorescent dye.

4. The system of claim 1 wherein:

the first light sensor includes a light pipe cover wherein the light pipe cover includes a fluorescent dye.

5. The system of claim 1 wherein:

the first light sensor includes a photo cell receptive to the wavelength of light.

6. The system of claim 1 wherein:

the first light sensor includes a light pipe wherein the light pipe contains a fluorescent dye that fluoresces and produces generally green light.

7. The system of claim 1 further comprising:

a control device in communication with the microprocessor for regulating the flow of water in response to the measured turbidity and microorganisms.

8. The system of claim 1 further comprising:

includes a second light sensor for sensing UV and visible light passing through filtered water in the water flow path.

9. The system of claim 1 further comprising:

a third light sensor located upstream of the filter;

a second water flow path located upstream of the filter and generally between the UV light source and the third light sensor;

wherein the third light sensor senses visible light passing through the second water flow path to determine turbidity of water entering the filter.

10. The system of claim 9 wherein:

the third visible light sensors lacks a fluorescent dye.

11. The system of claim 1 wherein:

the first and reference light sensors includes a light pipe and a photocell wherein the slight pipe includes a fluorescent green dye.

12. A water treatment system for filtering and sterilizing water using a turbidity and microorganism sensing system comprising:

a filter filtering water flowing through a water flow path;

a UV light source irradiating water flowing through the water flow path;

at least one UV light sensor wherein the UV light sensor includes a light pipe and photocell, wherein the light pipe includes a water exposed surface and a non-water exposed surface wherein the non-water exposed surface contains a fluorescent green dye for converting UV light to visible light;

at least one visible light sensor lacking a fluorescent dye;

a microprocessor connected to the UV light sensor and the visible light sensor wherein the microprocessor compares the sensed UV and visible light intensities to a UV and visible light intensity standard and evaluates and distinguishes between the level of turbidity and the level of microorganisms within the water flowing through the water flow path;

an alarm connected to the microprocessor for signaling when the sensed UV and visible light intensities are substandard; and at least one valve in communication with the microprocessor for controlling the volume of water flowing through the water treatment system in response to the sensed UV and visible light intensities.

* * * * *